(12) United States Patent
Li (10) Patent No.: US 9,168,199 B2
(45) Date of Patent: Oct. 27, 2015

(54) HOUSEHOLD MEDICATED-BATH TREATMENT DEVICE

(76) Inventor: Jianhua Li, Beijing (CN)

( * ) Notice: Subject to any disclaimer, the term of this patent is extended or adjusted under 35 U.S.C. 154(b) by 618 days.

(21) Appl. No.: 13/442,420

(22) Filed: Apr. 9, 2012

(65) Prior Publication Data
US 2013/0267890 A1 Oct. 10, 2013

(51) Int. Cl.
*A61H 35/00* (2006.01)
*A61H 33/00* (2006.01)
*A61M 35/00* (2006.01)
*A61M 3/02* (2006.01)
*A61H 33/06* (2006.01)

(52) U.S. Cl.
CPC ........ *A61H 33/0095* (2013.01); *A61H 33/6021* (2013.01); *A61H 35/00* (2013.01); *A61M 3/0225* (2013.01); *A61M 35/00* (2013.01); *A61H 2033/0079* (2013.01); *A61H 2033/061* (2013.01); *A61H 2033/068* (2013.01); *A61H 2201/0207* (2013.01); *A61H 2201/1633* (2013.01); *A61H 2201/50* (2013.01); *A61H 2201/5082* (2013.01); *A61H 2201/5097* (2013.01); *A61H 2205/086* (2013.01); *A61H 2205/087* (2013.01); *A61M 3/0258* (2013.01); *A61M 2205/3368* (2013.01); *A61M 2205/3561* (2013.01); *A61M 2205/3592* (2013.01); *A61M 2205/3653* (2013.01); *A61M 2209/01* (2013.01)

(58) Field of Classification Search
CPC ..................................................... A61H 33/06
USPC ............... 604/24, 26, 39, 514, 517, 131, 151, 604/289, 911; 4/420, 420.2, 420.3, 420.4, 4/420.5, 443–446, 615, 616, 536, 524, 4/525, 531, 532
See application file for complete search history.

(56) References Cited

U.S. PATENT DOCUMENTS

| 158,022 A | 12/1874 | Bremond |
| 4,206,520 A | 6/1980 | Fulford |
| 4,326,308 A | 4/1982 | Silver |
| 4,411,030 A * | 10/1983 | Kawai et al. ...................... 4/443 |
| 4,422,189 A * | 12/1983 | Couvrette ...................... 4/420.2 |
| 4,761,836 A * | 8/1988 | Tsutsui et al. .................. 4/420.2 |
| 4,862,526 A * | 9/1989 | Berger .............................. 4/536 |

(Continued)

FOREIGN PATENT DOCUMENTS

| CN | 2776387 Y | 5/2006 |
| CN | 2776387 Y * | 5/2006 |

*Primary Examiner* — Andrew Gilbert
(74) *Attorney, Agent, or Firm* — Porter, Wright, Morris & Arthur, LLP (57) ABSTRACT

A medicine-bath treatment device includes a central basin having a seat thereabout, at least one fumigation opening and at least one air opening, an inner vessel for holding liquid in fluid communication with the at least one fumigation opening of the basin to provide fumigation steam to the basin from the inner vessel, a spray tube having an inlet in communication with the inner vessel and an outlet in the basin to provide a jet of heated liquid within the basin, and a fan having an outlet in communication with the at least one air opening to provide a stream of heated drying air within the basin. The device also include a heater, a temperature sensor for measuring ambient air temperature, and a controller operably connected to the pump, the fan, and the heater. The controller is operably programmed to automatically adjust at least one of a treatment temperature of the jet of heated liquid, a treatment temperature of the fumigation steam, and a treatment temperature of the heated drying air based on the ambient air temperature.

20 Claims, 7 Drawing Sheets

(56) References Cited

U.S. PATENT DOCUMENTS

| | | | |
|---|---|---|---|
| 5,058,217 A * | 10/1991 | Taguchi et al. | 4/420 |
| 5,220,935 A | 6/1993 | Bailey et al. | |
| 5,898,956 A * | 5/1999 | Kurisaki et al. | 4/420.4 |
| 5,987,659 A | 11/1999 | Cannizzaro | |
| 6,105,178 A | 8/2000 | Kurisaki et al. | |
| 6,186,988 B1 | 2/2001 | Sabacinski et al. | |
| 6,968,580 B1 | 11/2005 | Chang Chien | |
| 7,051,382 B2 * | 5/2006 | Haberkorn | 4/420.4 |
| 7,849,528 B1 | 12/2010 | Tuday | |
| 7,886,373 B2 | 2/2011 | Kim | |
| 2003/0140407 A1 * | 7/2003 | Matsumoto et al. | 4/420.4 |
| 2005/0246828 A1 * | 11/2005 | Shirai et al. | 4/420.4 |
| 2007/0011802 A1 * | 1/2007 | Holland | 4/445 |
| 2007/0256225 A1 * | 11/2007 | Kim | 4/420.2 |
| 2009/0025131 A1 * | 1/2009 | Yamamoto et al. | 4/420 |
| 2012/0124730 A1 * | 5/2012 | Morotomi et al. | 4/443 |

\* cited by examiner

HOUSEHOLD MEDICATED-BATH TREATMENT DEVICE

CROSS-REFERENCE TO RELATED APPLICATIONS

Not Applicable

STATEMENT REGARDING FEDERALLY SPONSORED RESEARCH

Not Applicable

PARTIES TO A JOINT RESEARCH AGREEMENT

Not Applicable

REFERENCE TO APPENDIX

Not Applicable

FIELD OF THE INVENTION

The field of the present invention generally relates to methods and devices for administering therapeutic fluids and, more particularly, to such methods and devices for administering therapeutic fluids to treat anus and gynecological diseases and the like and/or provide personal care and cleanliness.

BACKGROUND OF THE INVENTION

Conventional therapy for common anus diseases, such as internal hemorrhoid, external hemorrhoid, mixed hemorrhoid, incarcerated hemorrhoid, perianal abscess, anal sinusitis, and the like, and common gynecological diseases, such as nonspecific colpitis (like colpitis mycotica, bacterial colpitis, candidal colpitis, gonococcal colpitis, and eczema of vulva), cervicitis, cervical erosion, pelvic inflammation, acute urethritis, and the like, are often treated with medicated or non-medicated warm tub or sitz baths, douching, antimicrobial suppositories, ointment application, and the like. Treatment devices having washing functions similar to bidets have been developed for the treatment of these types of diseases. However, these devices can be expensive so they are typically not available for household use.

Additionally, these conventional treatments and devices may not quickly and effectively alleviate or eliminate clinical symptoms of these diseases. Accordingly, there is a need in the art for improved method and device for treating anus and gynecological diseases and the like in a manner that enhances the absorption of a drug or the like to quickly alleviate or eliminate clinical symptoms.

SUMMARY OF THE INVENTION

Disclosed are methods and devices for treating anus and gynecological diseases and the like that overcome at least one of the disadvantages of the prior art described above. Disclosed is a medicine-bath treatment device comprising, in combination, a central basin having a seat thereabout, at least one fumigation opening and at least one air opening, an inner vessel for holding liquid in fluid communication with the at least one fumigation opening of the basin to provide fumigation steam to the basin from the inner vessel, a spray tube having an inlet in communication with the inner vessel and an outlet in the basin to provide a jet of heated liquid within the basin, a fan having an outlet in communication with the at least one air opening to provide a stream of heated drying air within the basin, a heater, a temperature sensor for measuring ambient air temperature, and a controller operably connected to the pump, the fan, and the heater. The controller is operably programmed to automatically adjust at least one of a treatment temperature of the jet of heated liquid, a treatment temperature of the fumigation steam, and a treatment temperature of the heated drying air based on the ambient air temperature.

Also disclosed is a medicine-bath treatment device comprising, in combination, a plastic housing forming central basin having a seat thereabout wherein the central basin has at one fumigation opening and at least one air opening, a metal inner vessel for holding liquid in fluid communication with the at least one fumigation opening of the basin to provide fumigation steam to the basin from the inner vessel, a pump having an inlet in fluid communication with the inner vessel and an outlet in fluid communication with a spray tube having an outlet in the basin to provide a jet of heated liquid within the basin, a fan having an outlet in communication with the at least one air opening to provide a stream of heated drying air within the basin, a heater, a temperature sensor for measuring ambient air temperature, and a controller operably connected to the pump, the fan, and the heater. The controller is operably programmed to automatically adjust at least one of a treatment temperature of the jet of heated liquid, a treatment temperature of the fumigation steam, and a treatment temperature of the heated drying air based on the ambient air temperature.

Also disclosed is a method of treatment comprising the steps of, in combination, providing a jet of heated liquid in a central basin having a seat thereabout to contact a patient sitting on the seat, providing fumigation steam in the basin to contact a patient sitting on the seat, providing a stream of heated drying air in the basin to contact a patient sitting on the seat, determining an ambient temperature, and automatically adjusting with a controller at least one of a treatment temperature of the jet of heated liquid, a treatment temperature of the fumigation steam, and a treatment temperature of the heated drying air based on the ambient air temperature.

From the foregoing disclosure and the following more detailed description of various preferred embodiments it will be apparent to those skilled in the art that the present invention provides a significant advance in the technology and art of medicated bath treatment devices. Particularly significant in this regard is the potential the invention affords for relatively inexpensive and effective methods and devices for treating anus and gynecological diseases and the like. Additional features and advantages of various preferred embodiments will be better understood in view of the detailed description provided below.

BRIEF DESCRIPTION OF THE DRAWINGS

These and further features of the present invention will be apparent with reference to the following description and drawing, wherein.

Figures 1, 2:
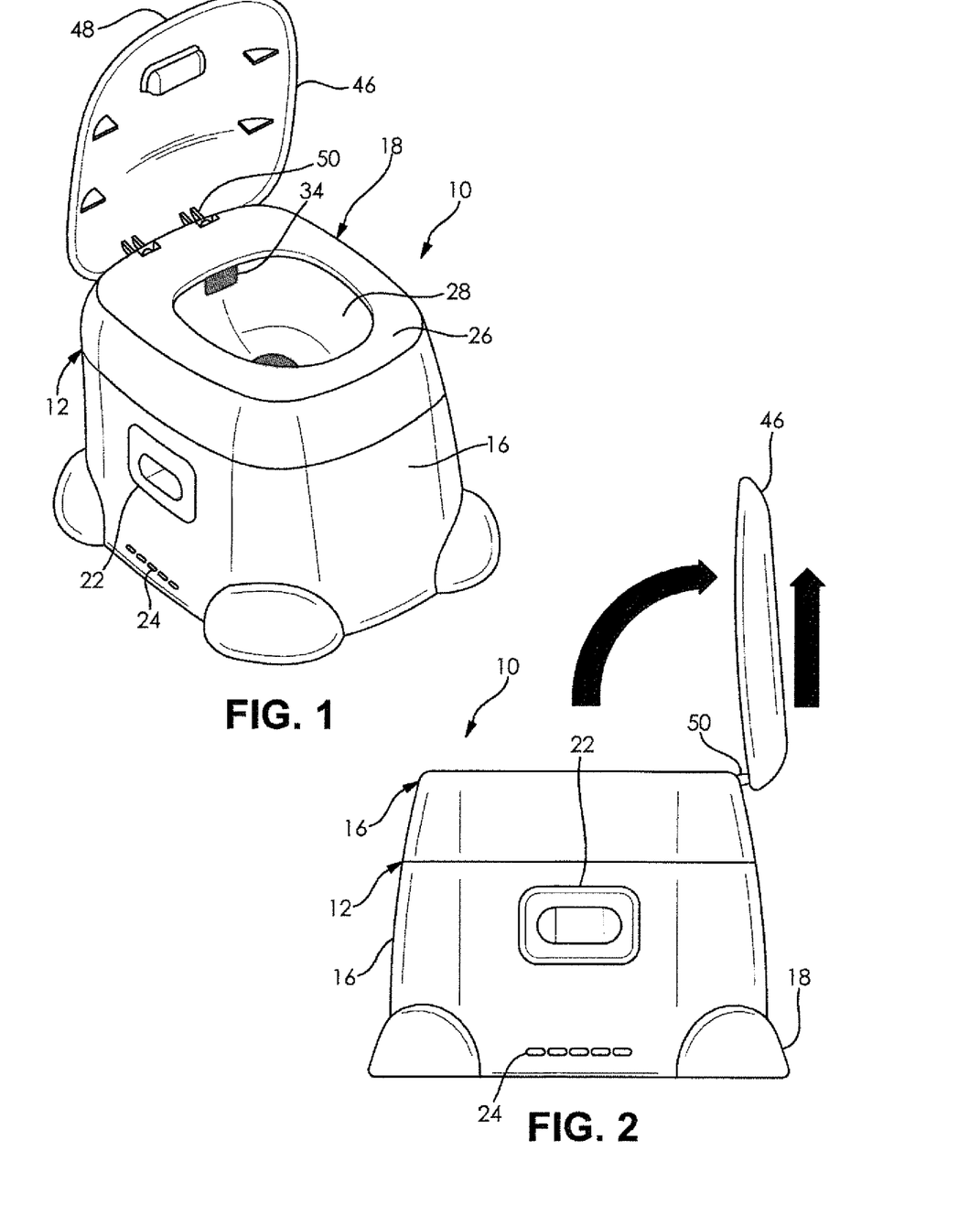
FIG. 1 is a front/right perspective view of a medicated-bath treatment device according to the present invention.
FIG. 2 is a left side elevational view of the treatment device of FIG. 1, wherein the removal of a cover is illustrated.
Figure 3:
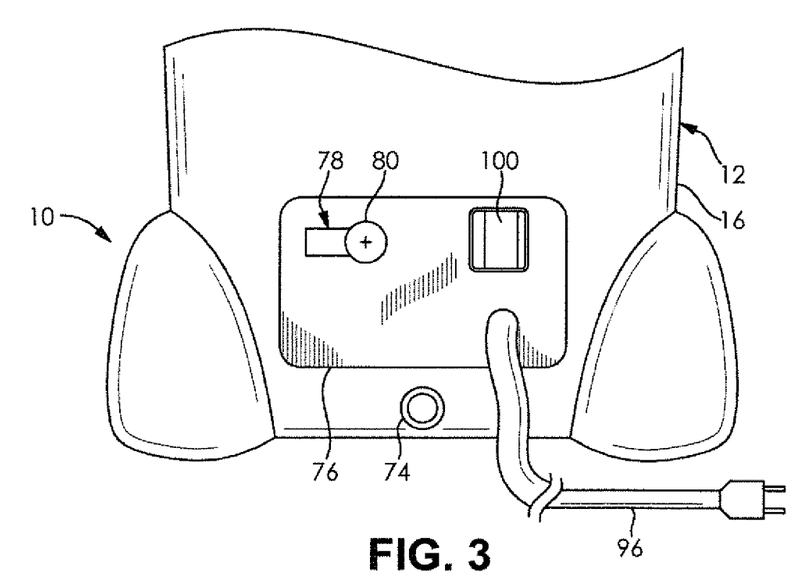
FIG. 3 is an enlarged, fragmented rear elevational view showing a rear control panel of the treatment device of FIGS. 1 and 2.
Figure 4:
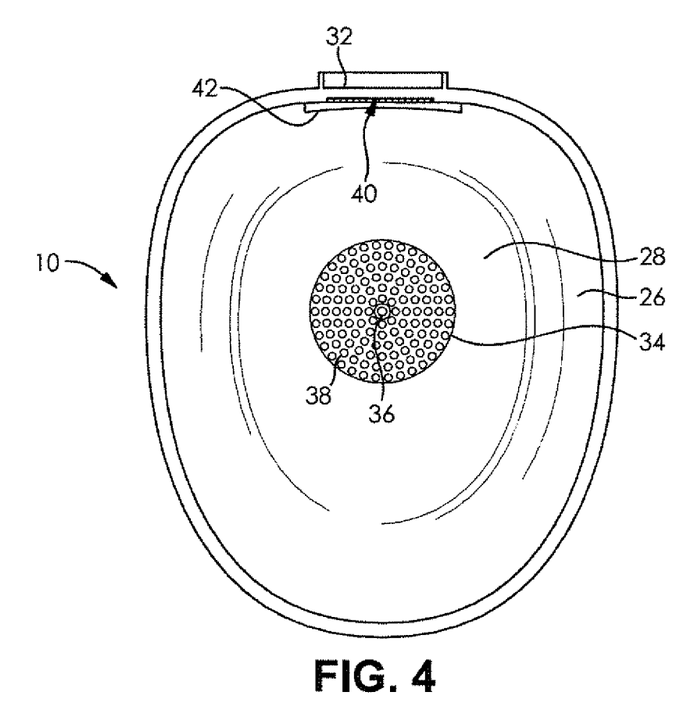
FIG. 4 is an enlarged top plan view of the treatment device of FIGS. 1 to 3.

It should be understood that the appended drawings are not necessarily to scale, presenting a somewhat simplified representation of various preferred features illustrative of the basic principles of the invention. The specific design features of the medicated-bath treatment devices as disclosed herein, including, for example, specific dimensions and shapes of the various components will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the medicated-bath treatment devices illustrated in the drawings. In general, front or forward generally refers to a direction to the left within the plane of the paper in FIG. 2 and back or rearward generally refers to a direction to the right within the plane of the paper in FIG. 2. Also in general, up or upward generally refers to an upward direction within the plane of the paper in FIG. 2 and down or downward generally refers to a downward direction within the plane of the paper in FIG. 2.

DETAILED DESCRIPTION OF CERTAIN PREFERRED EMBODIMENTS

It will be apparent to those skilled in the art, that is, to those who have knowledge or experience in this area of technology, that many uses and design variations are possible for the improved medicated-bath treatment devices and methods disclosed herein. The following detailed discussion of various alternative and preferred embodiments will illustrate the general principles of the invention with regard to the specific application of household medicated-bath treatment devices and methods. Other embodiments suitable for other applications will be apparent to those skilled in the art given the benefit of this disclosure, such as where the treatment device is in the form of a bed or chair. For example, see Chinese Patent Number CN2776387 Y.

FIGS. 1 to 7 illustrate a household medicated-bath treatment device 10 according to the present invention. The illustrated treatment device 10 has a housing 12 forming a hollow interior space 14. The illustrated housing 12 includes a main body 16 having an open top and an open bottom, an upper panel 18 generally closing the open top of the main body 16 and a lower panel 20 closing the open bottom of the main body 16. The illustrated main body, upper panel, and lower panel (16, 18, 20) are each molded of a plastic but it is noted that any other suitable material and method of manufacture can alternatively be utilized. The illustrated main body 16 is provided with integral hand holds or handles 22 formed therein on lateral sides. The illustrated main body 16 is provided with a plurality of vent openings 24 formed therein near the bottom of the lateral sides. The illustrated upper panel 18 is secured to the main body 16 with mechanical fasteners but can alternatively be attached in any other suitable manner or can be formed as a single component with the main body 16. The illustrated upper panel 18 forms a seat 26 with a central basin 28 formed therein. The illustrated basin 28 has a liquid opening 30 formed at a bottom thereof and a drying air or vent opening 32 formed at an upper rear edge thereof. The illustrated liquid opening 30 is provided with a metal plate 34 having a central nozzle opening 36 and a plurality of fumigation openings 38 surrounding the nozzle opening 36 as described in more detail hereafter. The illustrated air vent opening 32 is provided with a metal plate 40 having a plurality of air openings 42 as described in more detail hereafter. The illustrated lower panel 20 is secured to the main body 16 with mechanical fasteners but can alternatively be attached in any other suitable manner or can be formed as a single component with the main body 16. The illustrated lower panel 20 is provided with four rollers or casters 44 near its corners so that the treatment device 10 can be selectively rolled along the floor when desired.

The treatment device 10 also includes a removable cover 46 that is pivotally attached to a rear upper edge of the housing 12 so that the cover 46 can be pivoted down to cover the basin 28 and pivoted up about pivots or hinges to expose the basin 28. The illustrated cover 46 is molded of a plastic but it is noted that any other suitable material and method of manufacture can alternatively be utilized. The illustrated cover 46 has a hand hold or handle 48 integrally molded therein near a forward edge thereof. To remove the cover 46 for use of the treatment device 10, the cover 46 is pivoted up to a vertical orientation and then raised out of the hinges 50 to separate the cover 46 from the housing 12 (best shown in FIG. 2). The cover 46 can then be laid aside during use of the treatment device 10 and re attached in a reverse manner once use of the treatment device 10 is complete. It is noted that the cover 46 can alternatively have any other suitable form.

Figure 8:
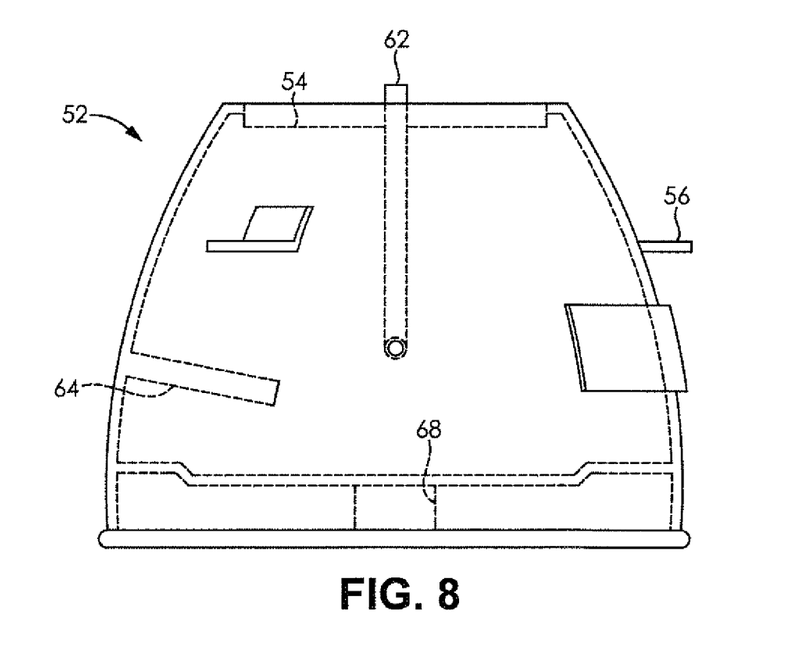
FIG. 8 is a left side elevational view of a inner basin assembly of the treatment device of FIGS. 1 to 7.
Figure 9:
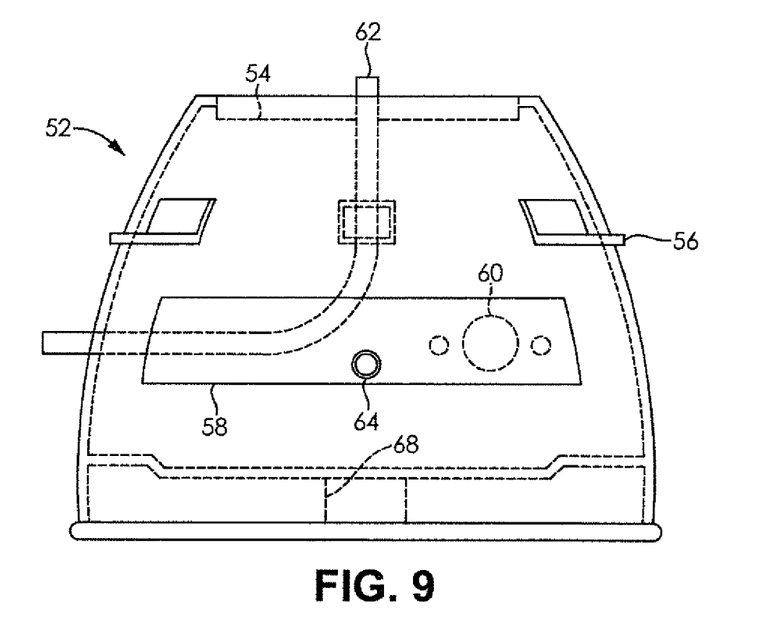
FIG. 9 is a front elevational view of the inner basin assembly FIG. 8.
Figure 10:
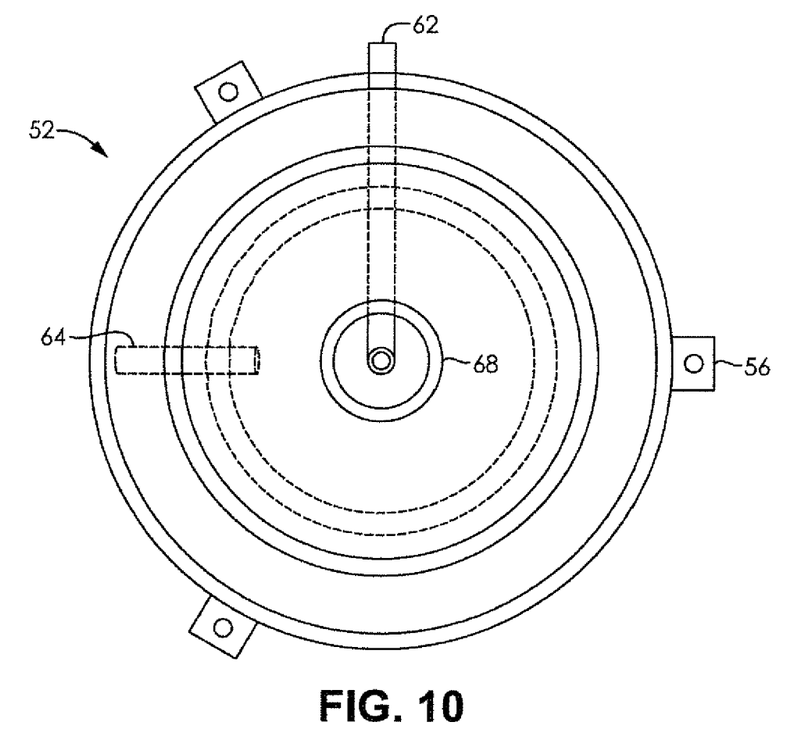
FIG. 10 is a bottom view of the inner basin assembly FIGS. 8 and 9.

The illustrated treatment device 10 includes an inner container or vessel 52 for holding treatment liquid. As best shown in FIGS. 8 to 10, the illustrated inner vessel 52 forms a hollow interior and is generally bell shaped having an outer wall that is circular in cross-section with the lower end having a larger diameter than the upper end. The illustrated inner vessel 52 comprises stainless steel but any other suitable material can alternatively be utilized. The upper end of the inner vessel 52 forms an upper opening 54 that cooperates with the liquid opening 30 of the basin 28 so that there is fluid combination between the basin 28 and the interior of the inner vessel 52. The illustrated outer wall is provided with a plurality of flanges 56 for securing the inner vessel 52 to the housing 12 within the interior space with mechanical fasteners but the inner vessel 52 can alternatively be secured to the housing 12 in any other suitable manner. The illustrated outer wall is also provided with a flange 58 for mounting at least one agitator 60 thereto to ensure mixing of treatment liquid within the inner vessel 52. A nozzle or spray tube 62 extends horizontally through the side wall at a left-hand side and bends to extend vertically at the central axis through the opening 54 in the upper end and through the central nozzle opening 36. A temperature sensor tube 64 extends angularly downward through the side wall at a forward side so that it contacts treatment fluid within the inner vessel 52. The illustrated temperature sensor tube 64 is closed at its inner end and is sized and shaped to receive a temperature sensor 66 for measuring the temperature of treatment liquid within the inner vessel 52. The lower end of the inner vessel 52 is generally closed by a lower wall except for a central opening 68. The illustrated lower wall is provided with a heater or heating means 70 for heating the treatment liquid within the inner vessel 52. The illustrated heater 70 is an electrical heater secured to the outer side of the lower wall but any other suitable heater 70 can alternatively be utilized.

Figure 5:
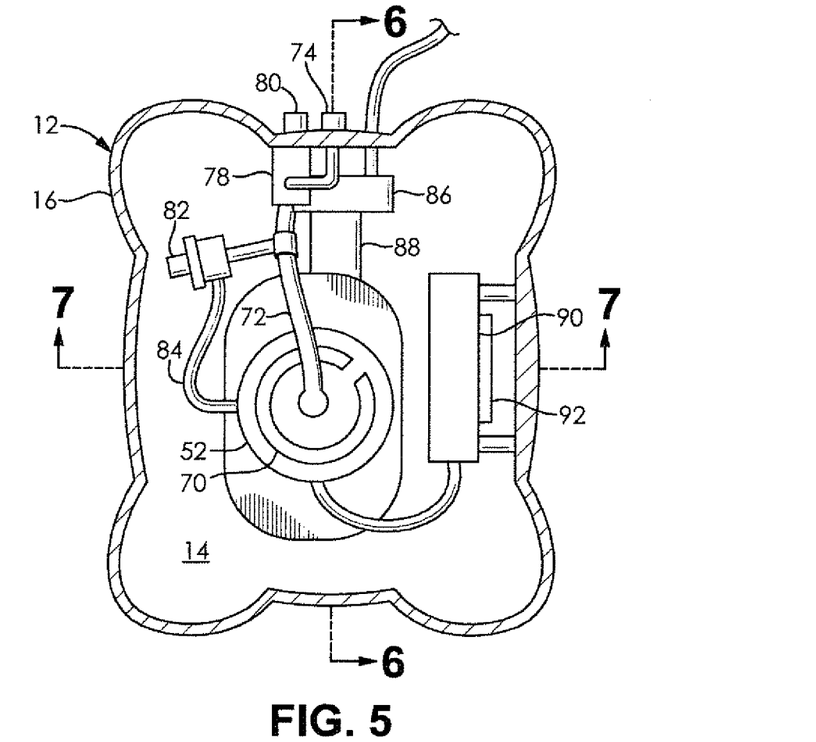
FIG. 5 is an enlarged bottom plan view of the treatment device of FIGS. 1 to 3, wherein a bottom panel of the housing and electrical wiring has been removed for clarity.
Figure 6:
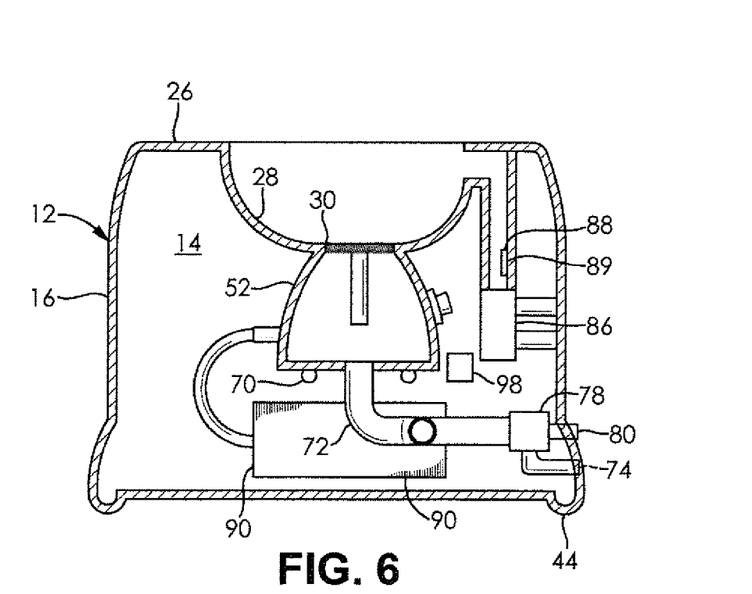
FIG. 6 is a cross sectional view taken along line 6-6 of FIG. 5.
Figure 7:
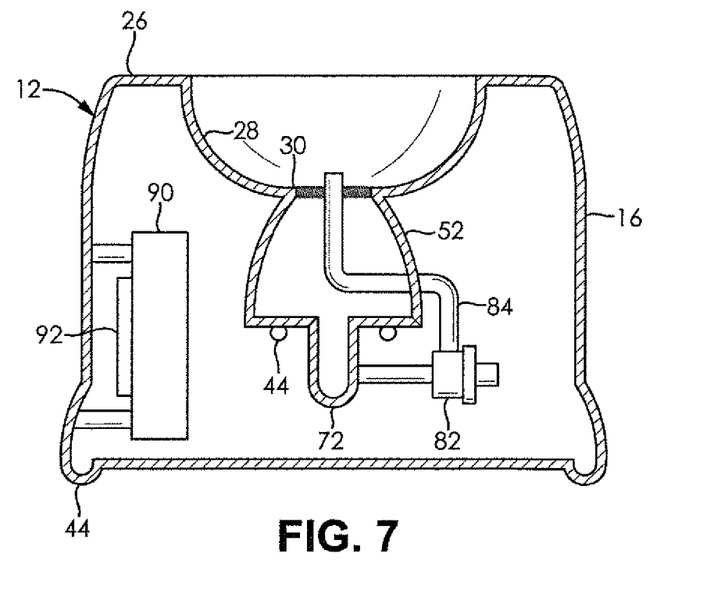
FIG. 7 is a cross sectional view taken along line 7-7 of FIG. 5.

As best shown in FIGS. 5 to 7, a tube or conduit 72 connects the opening 68 in the lower wall with a drain orifice 74 which extends through the housing 12 at a control panel 76 located near the bottom of the rear side of the housing 12. A manually operated drain valve 78 is provided near the drain orifice 74 to selectively open and close the drain orifice 74. A pivoting lever 80 of the drain valve 78 is located on the control panel 76. An inlet of an electric pump 82 is connected to the conduit 72 between the lower wall opening 68 and the drain valve 78. An outlet of the pump 82 is connected by a hose 84 to the inlet of the spray tube 62. The pump 82 is sized and configured to provide a desired variety of flow rates and spray heights for the treatment liquid from the spay tube 62 as describe in more detail hereinafter.

An electric fan 86 is secured to a rear wall of the housing 12 within the interior space 14. An inlet of the fan 86 receives air from within the housing interior space 14 and an outlet of the fan 86 is connected to a conduit or duct 88 that extends to the air vent opening 32 in the basin 28. The illustrated duct 88 has a heater or air heating means 89 provided therein to heat the air passing through the duct 88 to a desired treatment temperature. The illustrated heater 89 is an electrical heater secured within the duct 88 but any other suitable heater 89 can alternatively be utilized. When operating, the fan 86 pulls air from within the housing interior space 14 into the duct 88 and blows the heated air out of the air vent opening 32 into the basin 28 as described in more detail herein after.

The temperature sensor 66 is provided within the temperature sensor tube 64 to provide an indication of the temperature of the treatment fluid within the inner vessel 52. The temperature sensor 66 can be of any suitable type.

Figure 11:
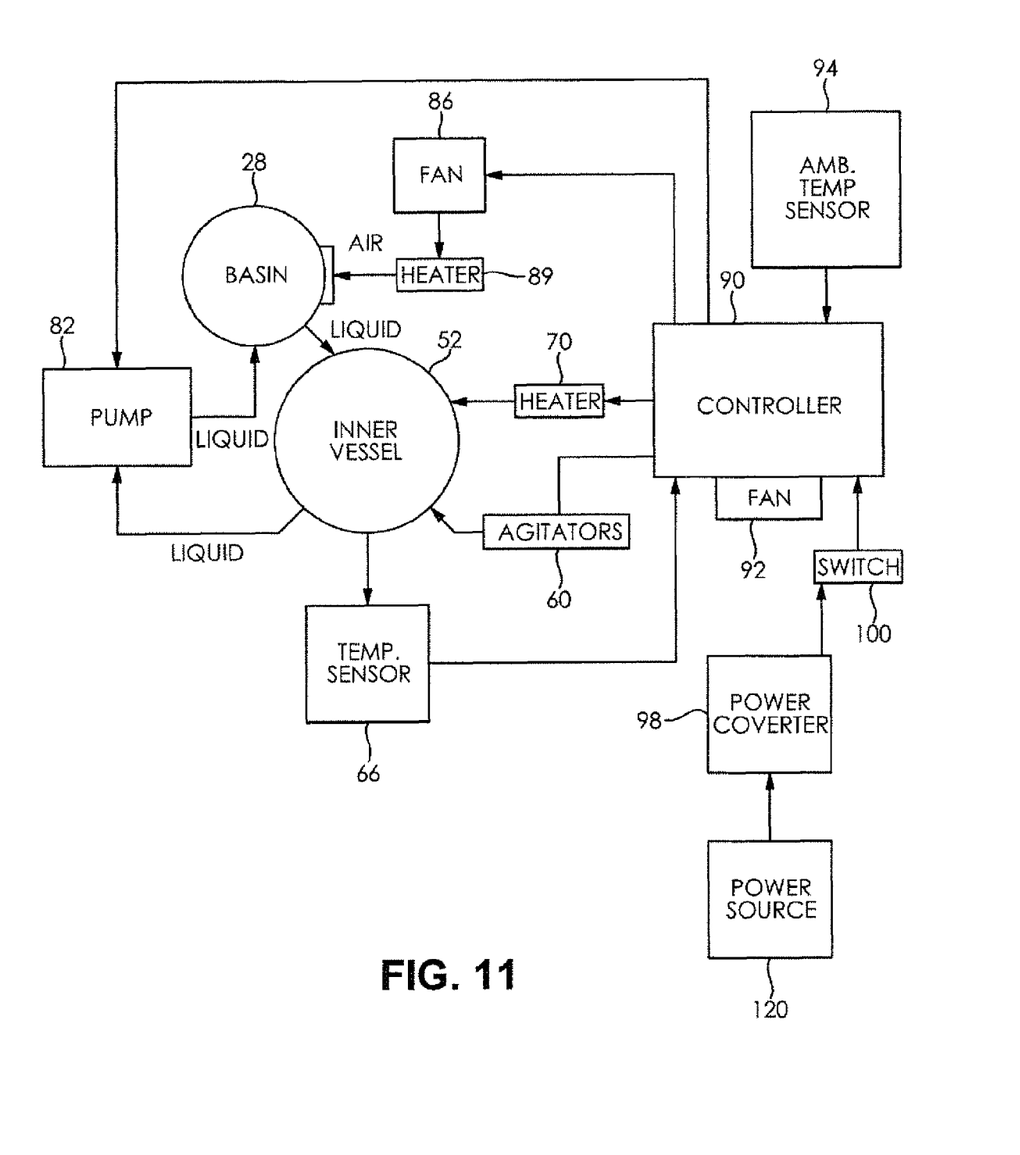
FIG. 11 is a diagrammatic view of the treatment device of FIGS. 1 to 7.

An electronic controller 90 comprising suitable memory and processing means is secured to the left side wall of the housing 12 within the interior space 14. The illustrated controller 90 is provided with a cooling fan 92. The controller 90 is also provided with an ambient temperature sensor 94 for providing signals indicating the ambient air temperature surrounding the treatment device 10. The illustrated controller 90 is operably connected to the agitator 60 to activate the agitator 60 when desired to mix the treatment liquid within the inner vessel 52. The illustrated controller 90 is operably connected to the heater 70 to activate the heater 70 when desired to heat the treatment liquid in the inner vessel 52 to a constant predetermined treatment temperature. The illustrated controller 90 is operably connected to the pump 82 to pump treatment liquid from the inner vessel 52 to the spray tube 62 when desired to spray the patient with treatment fluid at constant predetermined treatment temperature. The illustrated controller 90 is also operably connected to the fan 86 and the heater 89 to blow heated drying air into the basin 28 at a constant predetermined treatment temperature when desired to dry the patient.

An AC power cord 96 extends from the control panel 76 and is operably connected to an AC/DC power converter 98. The illustrated AC/DC power converter 98 is secured to the left side wall of the housing 12 within the interior space 14 near the controller 90. The AC/DC power converter 90 is operably connected to the controller 90 to provide electrical power thereto. A power on/off switch 100 is provided at the control panel 76 for selectively providing electrical power to the controller 90.

Figure 12:
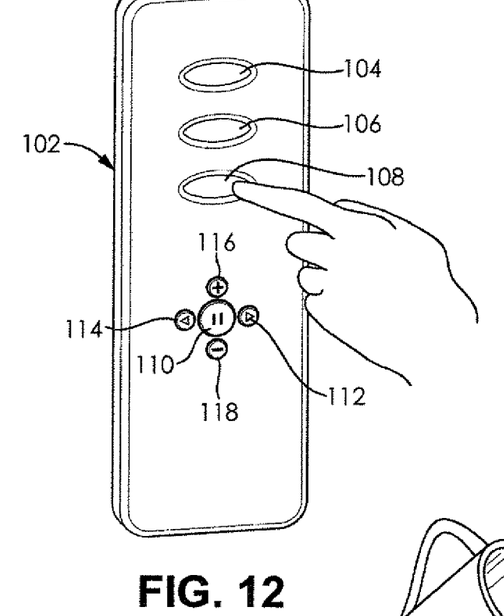
FIG. 12 is a perspective view of a wireless controller of the treatment device of FIGS. 1 to 11.

A wireless input device or remote control 102 is provided for inputting control signals to the controller 90. The illustrated remote control 102 has a first or medicate button or switch 104 for activating a spray sequence as described in more detail hereinbelow, a second or fumigate button or switch 106 for activating a spray sequence as described in more detail hereinbelow, and a third or dry button or switch 108 for activating a drying sequence as described in more detail hereinbelow. The illustrated remote control 102 also includes a pause button or switch 110, up and down buttons 112, 114 for increasing and decreasing the temperature of the treatment liquid respectively, and up and down buttons 116, 118 for increasing and decreasing the height of the spray of the treatment liquid respectively. It is noted that the remote control 102 can alternatively have any other suitable combination control functions. It is also noted that the remote control 102 can alternatively be wired or its functions can be integrated into the control panel 76 or a second control panel on the housing 12.

Figure 13:
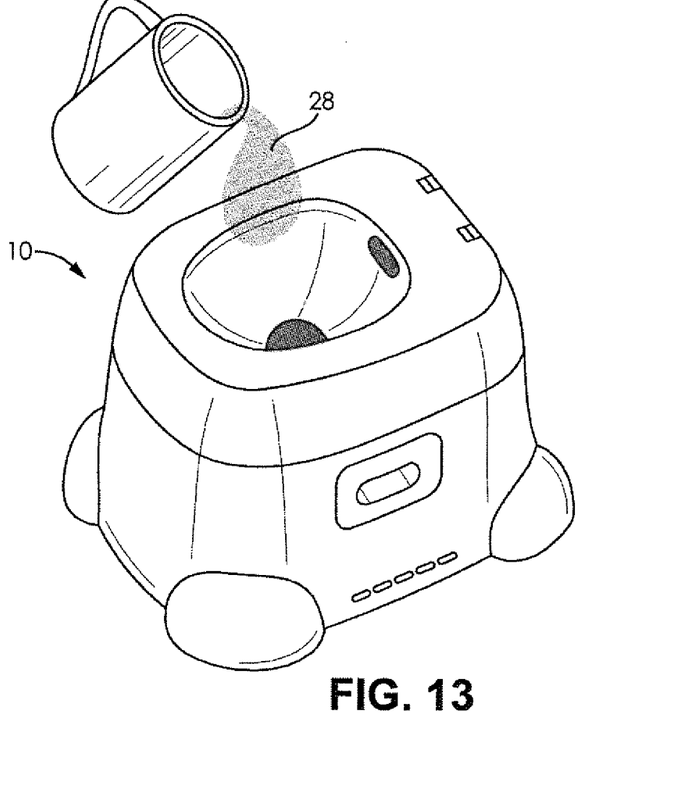
FIG. 13 is a diagrammatic view of the treatment device of FIGS. 1 to 12 being filled with a treatment liquid.

To operate the treatment device 10, the cover 46 is pivoted up and removed by raising it off of the housing 12. The cover 96 can then be laid aside. The drain valve 78 should be checked to make sure that the drain orifice 74 is closed or off. The power cord 96 is then connected to an AC power source 120 and the power switch 100 is turned on to power the treatment device 10. As best shown in FIG. 13, a suitable amount of treatment liquid is poured into the basin 28 so that it drains through the openings 38 and into the interior vessel 52. The treatment liquid can be clean water or mild water and can include filtered liquid medicine. A suitable amount of treatment liquid for the illustrated embodiment is 800 ml. The treatment liquid can be clean water or mild water and can include filtered liquid medicine. For example, the treatment liquid can be 800 ml containing 50 ml of filtered liquid medicine. The liquid medicine can be a Chinese herbal treatment or any other suitable liquid medicine or treatment.

The treatment device 10 automatically enters a heating or preheating stage wherein the controller 90 activates the heater 70 to heat the treatment liquid in the inner vessel 52. The preheating is complete after a predetermined period of time such as, for example, 5 minutes. A predetermined treatment temperature for the treatment liquid and/or air is determined based on the type of treatment (medicate, fumigate, dry) selected. The ambient air temperature is measured using the ambient temperature sensor 94 and it is determined whether the treatment temperature should be adjusted due to the ambient air temperature. The illustrated device is programmed to operate within an ambient temperature range of 20 degrees C. to 40 degrees 40 but any other suitable range can alternatively be utilized. The controller 90 is programmed with predetermined adjustments for the predetermined treatment temperatures based on the ambient air temperature. For example, if the ambient temperature is high relative to a predetermined normal ambient temperature, the treatment temperature is adjusted in an upward direction a predetermined amount. Also for example, if the ambient temperature is low relative to the predetermined normal ambient temperature, the treatment temperature is adjusted in an downward direction a predetermined amount. The predetermined adjustments can be linear or nonlinear relative to the ambient temperature as desired. The controller 90 then powers the heater 70 or heater 89 to raise the temperature of the treatment liquid or air to the adjusted treatment temperature. In one embodiment of the device 10, the controller 90 is operably programmed to automatically adjust each of a treatment temperature of the jet of heated liquid in the jet stage, a treatment temperature of the fumigation steam in the fumigation stage, and a treatment temperature of the heated drying air in the drying stage based on the ambient air temperature. In another embodiment of the device 10, the controller 90 is operably programmed to automatically adjust only a treatment temperature of the heated drying air in the drying stage based on the ambient air temperature. It is noted that the controller can be programmed to adjust any combination of the predetermined treatment temperatures based on the ambient air temperature as long as at least one of the predetermined treatment temperatures is adjusted based on the ambient air temperature.

The patient then sits on the seat 26 and selects a desired treatment function or stage (jet, fumigate, dry) using the remote control 102. If the medicate button 104 is pushed, the pump 82 is activated by the controller 92 to pump heated treatment liquid from the inner vessel 52 to the spray tube 62 where it is vertically sprayed out of the spray tube 62 and onto the patient sitting above the outlet of the spray tube 62. The illustrated jet treatment temperature is about 35 degrees C. unless adjusted due to the ambient temperature but any other suitable jet treatment temperature can alternatively be utilized. The jet treatment temperature is preferably in the range of about 32 to 38 degrees C. but any other suitable range can alternatively be utilized. For a higher or lower temperature, the patient can push the temperature up and down buttons 112, 114 respectively. For a higher or lower jet or stream height of the treatment liquid, the patient can push the height up and down buttons 116, 118 respectively. The patient can suspend the liquid jet by pushing the pause button 110. The controller 90 automatically stops the liquid jet after a predetermined period of time. The default time of the illustrated embodiment is about 6 minutes (6 minutes+/−5 seconds) but any other suitable default time can alternatively be utilized. After the completion of the liquid medicine jetting stage, the controller 90 automatically proceeds to the drug fumigation stage. If the patient wants to stop the liquid medicine jetting stage before reaching the default time and to proceed to the fumigation or drying stage, the patient only needs to press the fumigate button 106 or the dry button 108.

The fumigation stage can be used automatically after the liquid medicine jetting stage, or immediately upon starting treatment. The patient simply needs to push the fumigate button 106 to start the fumigation stage. During the fumigation stage, the controller 90 heats the treatment liquid within the inner vessel 52 to a predetermined treatment temperature produce continuous medicine steam at constant temperature which rises through the fumigation openings 38 in the bottom of the basin 28 to contact the patient sitting on the seat 26. The illustrated fumigation temperature is about 45 degrees C. unless adjusted due to the ambient temperature but any other suitable treatment temperature can alternatively be utilized. The fumigation treatment temperature is preferably in the range of about 45 to 75 degrees C. but any other suitable range can alternatively be utilized. For a higher or lower fumigation temperature, the patient can push the temperature up and down buttons 112, 114 respectively. The patient can suspend the fumigation stage by pushing the pause button 110. The controller 90 automatically stops the fumigation stage after a predetermined period of time. The default time of the illustrated embodiment is about 12 minutes (12 minutes+/−5 seconds) but any other suitable default time can alternatively be utilized. After the completion of the medicine fumigation, the controller 90 automatically proceeds to the drying stage. If the patient wants to stop the medicine fumigation before completion of the default time and proceed to the drying stage, the patient only needs to press the dry button 108.

The drying stage can be used automatically after the medicine fumigating stage, or immediately upon starting treatment. The patient simply needs to push the dry button 108 to start the drying stage. During the drying stage, the controller 90 powers the fan 86 and the heater 89 to produce a continuous steam of hot air at a constant predetermined treatment temperature through the air openings 42 in the back of the basin 28 to the patient. The drying treatment temperature is determined based on the ambient air temperature so that the higher the higher the ambient temperature, the higher the drying temperature. For an ambient temperature of about 20 to 40 degrees C., the illustrated drying treatment temperature is about 45 degrees C. to 80 degrees C. For a higher or lower drying treatment temperature, the patient can push the temperature up and down buttons 112, 114 respectively. The patient can suspend the drying stage by pushing the pause button 110 at any time. The controller automatically stops the drying stage after a predetermined period of time.

Once complete, the patient turns off power to the treatment device 10 with the power switch 100 and unplugs the power cord 96 from the power source 120. The treatment device 10 is then transported to a place where sewage can be discharged such as a toilet, tub or sink. The drain valve lever 80 is turned to its open position so that all remaining liquid within the treatment device 10 automatically drains out of the treatment device 10 through the drain orifice 74. The cover 26 can then be placed back onto the housing 12.

The illustrated device 10 is designed with multiple protections in order to prevent scalding due to overheating of liquid or air. First, if a user feels that a temperature is too high, the user can press the pause button 110 to pause the flow of heated liquid or air. Second, when a liquid temperature exceeds a rated temperature, the controller is programmed to stop jetting of heated fluid. Third, when the temperature of the liquid is higher than or equal to a rated temperature, a temperature control device independent of the control program will enforce jetting. Finally, if the heater 70 has a phenomenon of dry-heating due to the lack of water for any reason, the controller 90 automatically stops the heater 90 in order to avoid damage to the device 10.

Any of the features or attributes of the above described embodiments and variations can be used in combination with any of the other features and attributes of the above described embodiments and variations as desired.

From the foregoing disclosure it will be apparent that the treatment device can additionally be used for personal cleanliness and care and adjuvant therapy before and after surgery.

From the foregoing disclosure and detailed description of certain preferred embodiments, it will be apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:
1. A medicine-bath treatment device comprising, in combination:

a central basin having a seat thereabout, at least one fumigation opening at a bottom of a central opening and at least one air opening;

an inner vessel for holding treatment liquid below the central basin and having an upper opening in fluid communication with the at least one fumigation opening of the central basin to provide fumigation steam to the central basin from the inner vessel;

a spray tube having an inlet in communication with the inner vessel and an outlet in the central basin to provide a jet of heated treatment liquid from the inner vessel within the central basin;

a pump configured to selectively pump the treatment liquid from the inner vessel and through the spray tube into the central basin;

a fan having an outlet in communication with the at least one air opening to provide a stream of heated drying air within the central basin;

a heater configured to selectively heat the treatment fluid within the inner vessel;

a temperature sensor for measuring ambient air temperature;

a controller operably connected to the pump, the fan, and the heater; and wherein the controller is operably programmed to provide predetermined treatment temperatures for the jet of heated treatment liquid, the fumigation steam, and the heated drying air and to automatically adjust at least one of the predetermined treatment temperatures for the jet of heated treatment liquid, the fumigation steam, and the heated drying air based on the ambient air temperature by adjusting the at least one of the predetermined treatment temperatures in an upward direction a predetermined amount when the ambient air temperature is above a predetermined normal ambient temperature and by adjusting the at least one of the predetermined treatment temperatures in a downward direction a predetermined amount when the ambient air temperature is below the predetermined normal ambient temperature.

2. The medicine-bath treatment device according to claim 1, wherein the controller is operably programmed to automatically adjust each of the predetermined treatment temperatures of the jet of heated treatment liquid, the fumigation steam, and the heated drying air based on the ambient air temperature.

3. The medicine-bath treatment device according to claim 1, wherein the controller is operably programmed to automatically adjust the predetermined treatment temperature of the heated drying air based on the ambient air temperature.

4. The medicine-bath treatment device according to claim 3, wherein the controller is operably programmed to automatically adjust only the predetermined treatment temperature of the heated drying air based on the ambient air temperature.

5. The medicine-bath treatment device according to claim 1, wherein the central basin comprises plastic.

6. The medicine-bath treatment device according to claim 5, wherein the inner vessel comprises metal.

7. The medicine-bath treatment device according to claim 1, further comprising a removable cover to cover the seat and the central basin when the medicine-bath treatment device is not in use.

8. The medicine-bath treatment device according to claim 7, wherein the removable cover comprises plastic.

9. The medicine-bath treatment device according to claim 1, further comprising a remote control in communication with the controller.

10. A medicine-bath treatment device comprising, in combination:

a plastic housing forming a central basin having a seat thereabout;

wherein the central basin has at least one fumigation opening at a bottom of the central basin and at least one air opening at an upper rear edge of the central basin;

a metal inner vessel for holding treatment liquid below the central basin and having an upper opening in fluid communication with the at least one fumigation opening of the central basin to provide fumigation steam to the central basin from the inner vessel;

a spray tube having an inlet in communication with the inner vessel;

wherein the spray upwardly extends through the upper opening of the inner vessel so that an outlet of the spray tube provides a jet of heated treatment liquid from the inner vessel within the central basin;

a pump having an inlet in fluid communication with the inner vessel and an outlet in fluid communication with the spray tube;

a fan having an outlet in communication with the at least one air opening to provide a stream of heated drying air within the central basin;

a heater configured to selectively heat the treatment fluid within the inner vessel;

a temperature sensor for measuring ambient air temperature;

a controller operably connected to the pump, the fan, and the heater; and wherein the controller is operably programmed to provide predetermined treatment temperatures for the jet of heated treatment liquid, the fumigation steam, and the heated drying air and to automatically adjust at least one of the predetermined treatment temperatures for the jet of heated treatment liquid, the fumigation steam, and the heated drying air based on the ambient air temperature by adjusting the at least one of the predetermined treatment temperatures in an upward direction a predetermined amount when the ambient air temperature is above a predetermined normal ambient temperature and by adjusting the at least one of the predetermined treatment temperatures in a downward direction a predetermined amount when the ambient air temperature is below the predetermined normal ambient temperature.

11. The medicine-bath treatment device according to claim 10, wherein the controller is operably programmed to automatically adjust each of the predetermined treatment temperatures of the jet of heated treatment liquid, the fumigation steam, and the heated drying air based on the ambient air temperature.

12. The medicine-bath treatment device according to claim 10, wherein the controller is operably programmed to automatically adjust the predetermined treatment temperature of the heated drying air based on the ambient air temperature.

13. The medicine-bath treatment device according to claim 12, wherein the controller is operably programmed to automatically adjust only the predetermined treatment temperature of the heated drying air based on the ambient air temperature.

14. The medicine-bath treatment device according to claim 10, further comprising a removable cover to cover the seat and the central basin when the medicine-bath treatment device is not in use.

15. The medicine-bath treatment device according to claim 14, wherein the removable cover comprises plastic.

16. The medicine-bath treatment device according to claim 10, further comprising a remote control in communication with the controller.

17. A method of treatment comprising the steps of, in combination:
providing a jet of heated treatment liquid in a central basin having a seat thereabout to contact a patient sitting on the seat;
providing fumigation steam in the central basin to contact the patient sitting on the seat;
providing a stream of heated drying air in the central basin to contact the patient sitting on the seat;
determining an ambient air temperature; and
automatically adjusting with a controller at least one of a predetermined treatment temperatures for the jet of heated treatment liquid, the fumigation steam, and the heated drying air based on the ambient air temperature by adjusting the at least one of the predetermined treatment temperatures in an upward direction a predetermined amount when the ambient air temperature is above a predetermined normal ambient temperature and by adjusting the at least one of the predetermined treatment temperatures in a downward direction a predetermined amount when the ambient air temperature is below the predetermined normal ambient temperature.

18. The medicine-bath treatment device according to claim 17, wherein the controller is operably programmed to automatically adjust each of the predetermined treatment temperatures of the jet of heated treatment liquid, the fumigation steam, and the heated drying air based on the ambient air temperature.

19. The medicine-bath treatment device according to claim 17, wherein the controller is operably programmed to automatically adjust the predetermined treatment temperature of the heated drying air based on the ambient air temperature.

20. The medicine-bath treatment device according to claim 19, wherein the controller is operably programmed to automatically adjust only the predetermined treatment temperature of the heated drying air based on the ambient air temperature.

* * * * *